(12) United States Patent
Shayne et al.

(10) Patent No.: US 11,350,243 B2
(45) Date of Patent: May 31, 2022

(54) LOCATION TRACKING

(71) Applicant: ObjectVideo Labs, LLC, Tysons, VA (US)

(72) Inventors: Ethan Shayne, Clifton Park, NY (US); Donald Gerard Madden, Columbia, MD (US)

(73) Assignee: ObjectVideo Labs, LLC, Tysons, VA (US)

( * ) Notice: Subject to any disclaimer, the term of this patent is extended or adjusted under 35 U.S.C. 154(b) by 0 days.

(21) Appl. No.: 17/150,278

(22) Filed: Jan. 15, 2021

(65) Prior Publication Data

US 2021/0219100 A1 Jul. 15, 2021

Related U.S. Application Data

(60) Provisional application No. 62/961,469, filed on Jan. 15, 2020.

(51) Int. Cl.
| | | |
|---|---|---|
| *H04W 4/029* | (2018.01) | |
| *H04W 4/021* | (2018.01) | |
| *A61B 5/024* | (2006.01) | |
| *G06F 3/01* | (2006.01) | |
| *G06V 20/00* | (2022.01) | |
| *G06V 40/10* | (2022.01) | |

(52) U.S. Cl.
CPC ......... *H04W 4/029* (2018.02); *A61B 5/02438* (2013.01); *G06F 3/011* (2013.01); *G06V 20/36* (2022.01); *G06V 40/10* (2022.01); *H04W 4/021* (2013.01)

(58) Field of Classification Search
CPC ..... H04W 4/029; H04W 4/021; H04W 4/024; A61B 5/02438; A61B 5/002; A61B 5/0046; A61B 5/02433; A61B 5/0261; A61B 5/1113; A61B 5/1128; A61B 5/117; A61B 5/681; A61B 5/7267; A61B 2560/0223; G06F 3/011; G06V 20/36; G06V 40/10; G06V 40/15; G06V 20/52; G06Q 90/20
See application file for complete search history.

(56) References Cited

U.S. PATENT DOCUMENTS 10,824,703 B1 * 11/2020 Desai ...................... G06F 21/32

* cited by examiner

*Primary Examiner* — Kabir A Timory
(74) *Attorney, Agent, or Firm* — Fish & Richardson P.C.

(57) ABSTRACT

Methods, systems, and apparatus, including computer programs encoded on computer-storage media, for location tracking. In some implementations, a corresponding method includes obtaining images of one or more persons within a property; identifying a heartbeat for each person of the one or more persons within the images; identifying a location for each person within the images; receiving a request that indicates a heartbeat signature generated from heartbeats sensed by a device worn by a user; determining that an identified heartbeat of a person of the one or more persons matches the heartbeat signature; in response to determining that the identified heartbeat of the person of the one or more persons matches the heartbeat signature, selecting the person as the user; and in response to selecting the person as the user, providing a response to the request based on a location of the person.

20 Claims, 2 Drawing Sheets

LOCATION TRACKING

CROSS-REFERENCE TO RELATED APPLICATION

This application claims the benefit of U.S. Provisional Application No. 62/961,469, filed on Jan. 15, 2020, the contents of which are incorporated by reference herein in its entirety.

BACKGROUND

A monitoring system for a property can include various components including sensors, cameras, and other devices. For example, the monitoring system may use the camera to capture images of people that enter the property.

SUMMARY

This specification describes techniques, methods, systems, and other mechanisms for locating and providing location information to the user. Tracking and directing users may be useful. For example, a system may be able to provide directions to a user that is lost based on tracking a location of the user.

Tracking and directing users may be done with multiple cameras that provide video of a room, floor, or section of an area. For example, a room may include a camera at each corner of the room where the four cameras together show all portions of the room. Each camera may be calibrated such that each pixel within a camera's field of view is mapped to a physical location. For example, a particular camera may be calibrated so that a pixel in a lower left corner corresponds to a geographical coordinate and a pixel in a lower right corner corresponds to another geographical coordinate.

Each camera may have the functionality to obtain a heartbeat signature of people within the field of view and use this data to identify users and provide locations. The functionality can involve transdermal imaging which may refer to the ability of a camera that is outside of a human body to capture images through a skin of a human. For example, each camera may capture images that show blood flow within human blood vessels. Images of blood flow can be used to detect a heartbeat. The functionality can also involve using lasers to detect heartbeat signatures. For example, a form of laser vibrometry can be used to detect movement caused by a heartbeat. A computer can process one or more signals from the laser to construct a heartbeat signature.

One implementation of a system that tracks users may allow users that want to know their location to use a wearable device to capture and send their heartbeat signature to the server as a location request. For example, a user may use a wrist worn watch that monitors their heartbeat to send a location request to a server where the location request includes timing of the last twenty heartbeats of the user. In some implementations, the wrist worn watch that monitors the heartbeat of a user may send heartbeat information to a smartphone of the user. The smartphone of the user can communicate with a server to request a location.

The server may then look for a match between the heartbeat signature received from the wearable device and the heartbeat signatures obtained through transdermal imaging, or other sensor data, of people within the field of view. For example, the server may determine that the timing of the last twenty heartbeats of the user matches timing of twenty heartbeats for a particular person shown in images.

After a match is made, the server may associate the user within the field of view of the cameras to the wearable device which requested the location. For example, the server may determine that the user that is requesting their location is the person in the images with the matching heartbeats.

The user's location within the field of view of a calibrated camera may then be translated to a location within a physical space. For example, the server may identify the pixels that show the feet of the person in the images that was matched, and then determine the geographical coordinates that match the pixels. This location may be sent to the device which sent the request. For example, the server may transmit a map to a smartphone that shows an indication of the user at the geographical coordinates on the map. In some cases, the server may transmit a location of a user which can be shown on a pre-existing map stored on a device. For example, the server may transmit a location of a user to a smartphone. The smartphone can plot the location of the user on a previously downloaded map of the interior of a location (e.g., airport, mall, etc.). The smartphone can graphically show the map of the interior of a location together with the location of the user.

In some implementations, more than one user location can be displayed on a single map. For example, a family at an airport can enroll within a system to receive location updates. A family member within the family can receive location updates for multiple family members which can be displayed on the map as multiple icons.

In another example, location monitoring within buildings may enable navigation for a user. For example, a user wanting to reach a specific store in a shopping mall may request their location from the system. The system may provide a location in the manner discussed above. The location may be used within a graphical representation of the mall on a user's device. Additional location data may be exchanged between the system and the user device, in the background, to aid in navigating the user to the specific store.

In one aspect, the disclosure provides a method that includes obtaining images of one or more persons within a property; identifying a heartbeat for each person of the one or more persons within the images of the one or more persons; identifying a location for each person within the images; receiving a request that indicates a heartbeat signature generated from heartbeats sensed by a device worn by a user; determining that an identified heartbeat of a person of the one or more persons matches the heartbeat signature; in response to determining that the identified heartbeat of the person of the one or more persons matches the heartbeat signature, selecting the person as the user; and in response to selecting the person as the user, providing a response to the request based on a location of the person.

In some implementations, the images include transdermal data of the one or more persons and identifying a heartbeat for each person of the one or more persons within the images of the one or more persons includes using the transdermal data of the one or more persons to determine patterns of blood flow; and in response to determining the patterns of blood flow, identifying a heartbeat for each person of the one or more persons.

In some implementations, the images include a first portion of one or more pixels that represent a first person and identifying a location for each person within the images includes determining the first portion of the one or more pixels correspond to a physical location of the property and the first portion of the one or more pixels represent at least a portion of the first person; and identifying the physical location of the property as a location of the first person of the one or more persons.

In some implementations, the physical location of the property is indicated by one or more geographical coordinates.

In some implementations, the method includes, before receiving the request, storing the identified heartbeat of the person within data storage, where determining that the identified heartbeat of the person of the one or more persons matches the heartbeat signature includes obtaining the identified heartbeat from the data storage; and comparing the heartbeat signature of the request to the identified heartbeat from the data storage to determine that the identified heartbeat of the person of the one or more persons matches the heartbeat signature.

In some implementations, determining that the identified heartbeat of the person of the one or more persons matches the heartbeat signature includes obtaining a first portion of the identified heartbeat and a second portion of the heartbeat signature, where the first portion includes at least a representation of a first heartbeat and the second portion includes at least a representation of a second heartbeat; determining that elements of a first cardiac cycle corresponding to the representation of the first heartbeat match elements of a second cardiac cycle corresponding to the representation of the second heartbeat; and determining that the identified heartbeat of the person of the one or more persons matches the heartbeat signature based at least on determining that the elements of the first cardiac cycle corresponding to the representation of the first heartbeat match the elements of the second cardiac cycle corresponding to the representation of the second heartbeat.

In some implementations, the request includes at least one visual identifier of the user that is used in selecting the person as the user.

In some implementations, the request includes a device identifier corresponding to a user device, and where providing the response to the request includes providing the response to the user device based on the device identifier.

In some implementations, the device worn by the user is a smart watch that senses blood flow within blood vessels of the user. In some implementations, the request is received from the device worn by the user. In some implementations, the device worn by the user is communicably connected to a mobile device of the user and the request is received from the mobile device of the user.

In some implementations, the property is an airport. In some implementations, the response to the request is used to provide the location of the person within the property to a mapping application operating on a user device.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
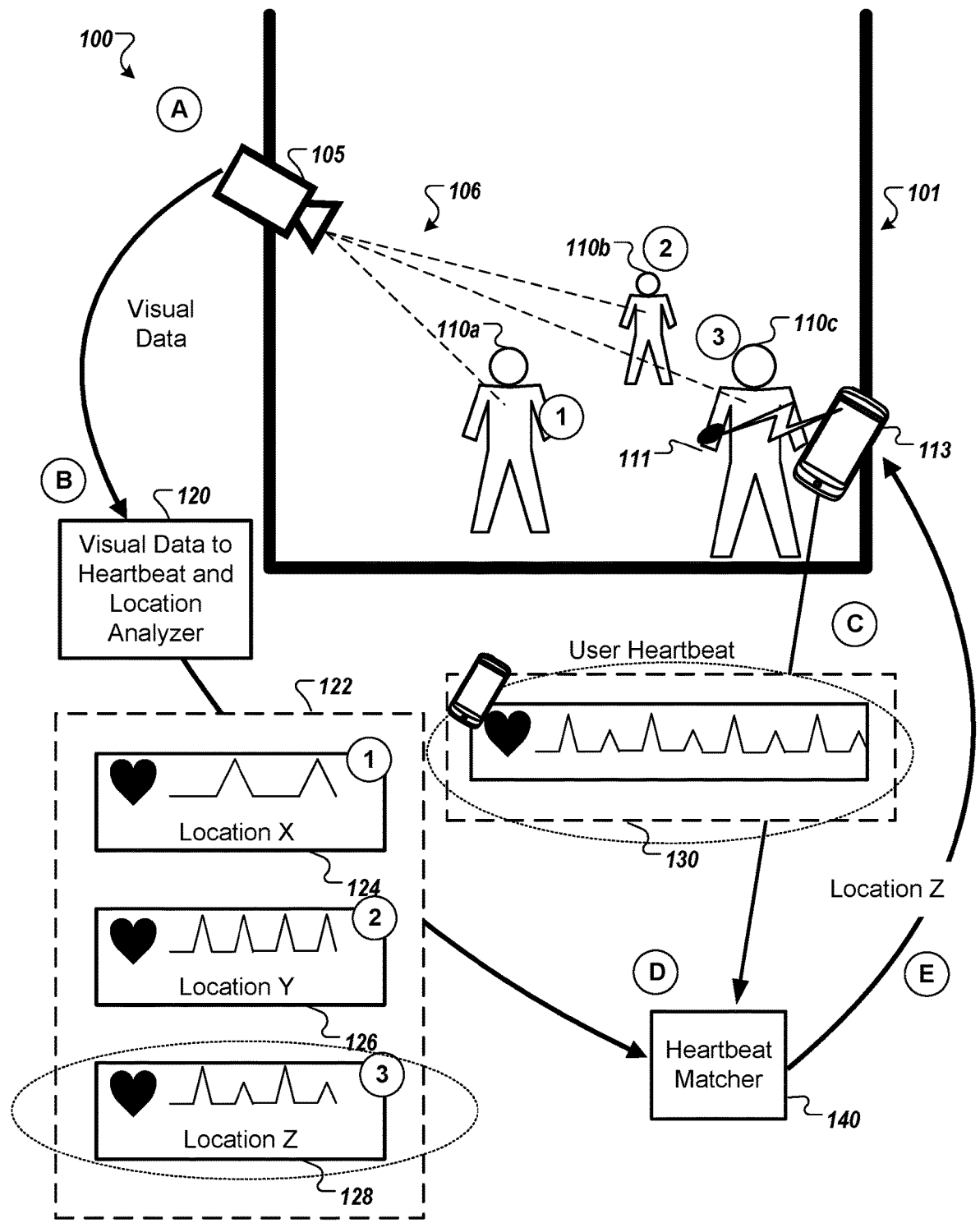
FIG. 1 is a diagram showing an example of a system for location tracking.

FIG. 1 is a diagram showing an example of a system 100 for location tracking. The system 100 includes a camera 105, a wearable device 111, a mobile computing device 113, a visual data to heartbeat and location analyzer 120, and a heartbeat matcher 140.

The camera 105 may be a device that captures transdermal images. For example, the camera 105 may be a transdermal image camera positioned so that it has a view of three people on a property.

The wearable device 111 may be a device worn by a user that captures the user's heartbeat. For example, the wearable device 111 may be a smart watch affixed to a wrist of user 110c measuring a heartbeat by sensing blood flow within blood vessels of the wrist.

The mobile computing device 113 may be a device on the person of a user. For example, the mobile computing device 113 may be a smartphone held by user 110c which can receive and transmit data signals.

The visual data to heartbeat and location analyzer 120 may be a computer program. For example, the visual data to heartbeat and location analyzer 120 may be a decision tree, neural network or rule based algorithm which can determine heartbeat and location based on input data. The program can be executed on any silicon based computer architecture. The computer architecture can be within the camera 105 or within an external system (e.g., server).

The heartbeat matcher 140 may be a computer program. For example, the heartbeat matcher 140 may be an algorithm or function that forms a match from a user to one of the persons observed by the system 100. The program can be executed on any silicon based computer architecture. The computer architecture can be within the camera 105 or within an external system (e.g., server).

Stage A in FIG. 1 shows a camera 105 connected within system 100 receiving visual data of people at location 101. Dashed lines 106 represent visual data of persons 110a, 110b, and 110c picked up on the image sensors of the camera 105.

Stage B of FIG. 1 depicts visual data from camera 105 analyzed in analyzer 120. The analysis first breaks down the data into persons within the field of view. For each person, both a heartbeat signature and location is calculated. Heartbeat signature may be read with the use of transdermal imaging or visual algorithms performed on video footage. Location may be processed by matching the location of the user within video footage to a location in physical space. The heartbeats and locations of users may be stored within system 100 and retrieved for a user location request.

In some implementations, visual data analysis can either be performed within the system 100 or remotely via a connected server. In locations or situations where privacy or security is a priority, the visual data to heartbeat and location analyzer 120 may be executed on a device or software within the system 100. In other implementations, it may be useful to process the data on a network using a server or other remote processor.

In some implementations, pixels within a camera's field of view can be mapped to actual locations in real world space. For example, an airport may have a camera in the entrance lobby. A generated map could take each pixel within the field of view of the airport entrance camera and map it to a particular place within the entrance lobby. This could be used to pinpoint the location of any object seen on video within physical space including a person.

In some implementations, visual analysis can register patterns within video footage and transform the visual data into a heartbeat signature. This can be used with different color light or alternate camera sensors (e.g., infrared) to detect heartbeat at a distance. For example, green light can be used to detect a presence of hemoglobin in the blood vessels of a person. Visual processing can convert the hemoglobin detection into a digital signal. Changes within this signal can be used to record a heartbeat signature. Hemoglobin detection can be used in collaboration with other visual analysis techniques to create a heartbeat signature.

In some implementations, a unique infrared signal from a smartphone or wearable can be used to identify a user. For example, a smartwatch of a user can transmit an infrared pulse at a specific frequency. The smartwatch can send a signature of the infrared pulse at the specific frequency along with a request for location data to a system. An infrared sensitive video camera within the system can detect the infrared pulse at the specific frequency. The system can match the infrared pulse detected by the infrared sensitive video camera to the signature of the infrared pulse sent within the request for location data. A match can be used to identify the user.

In some implementations, a device can transmit the infrared signal and another device can request location data from a system. For example, a smartwatch of a user can transmit an infrared pulse at a specific frequency. The smartwatch can send a signature of the infrared pulse to a smartphone of the user. The smartphone of the user can send the signature of the infrared pulse along with a request for location data to the system.

In some implementations, another form of visual data captured by the system 100 can be processed by a control unit as a form of identification for a user. For example, a user could use a terminal where they present a keycard or identification of some form. A control unit for system 100 can send a signal to other devices within system 100 to collect information from the keycard, or other identification (e.g., driver's license, passport, etc.), and use it to identify a user. Data can be passed to the identified user when requested.

In some implementations, a system can use heartbeat signatures to confirm the location of a user during an authentication process. For example, when a user is checking into a flight at a terminal, a smartphone, wearable, or other device can send a heartbeat signature to the system. The system can use functionality such as transdermal imaging to separately calculate a heartbeat signature of the user. The system can match the separately calculated heartbeat signature to the heartbeat signature sent to the system. A match can be used to confirm the identity and location of the user. In some cases, this can be used to aid in confirming an identity using identification documents (e.g., driver's license, passport, etc.) or other biometric data (e.g., fingerprint, retina scan, etc.).

In some implementations, a pre-determined location can be used to help locate a user. For example, a user when entering an airport can go to a kiosk. The user can enroll a device (e.g., smartphone, wearable, etc.) to receive location updates from a system. The system can use functionality such as transdermal imaging to detect a heartbeat signature of the user. The heartbeat signature of the user can be used to track the location of the user as they begin moving around. An enrolled device can be used to receive location updates sent from the system.

In some implementations, the system can save an association between a unique device identifier and a heartbeat signature used during enrollment. The heartbeat signature can be a heartbeat signature sent from a device of a user to the system or a heartbeat signature detected by the system from observing the user. The system can use the association between the unique device identifier and the heartbeat signature to aid in future location updates. For example, a device of a user could send a unique device identifier to a system. The system can have an association between the unique device identifier and a heartbeat signature of the user saved. The system can use the saved heartbeat signature of the user to locate the user. The system can send location updates to the device based on the unique device identifier.

In some implementations, the system can use an initial calibration of heartbeats to aid in future location updates. For example, a system can compare the heartbeat signature detected of a user with the heartbeat signature reported by a device of the user during enrollment. The user can move around in a location and request location updates by sending a heartbeat signature to a system. The system can use the calibration of heartbeats performed during an enrollment of the user to help locate the user.

In some implementations, a user can be presented with options by the system. The options can be presented when enrolling a device. For example, a user can choose whether or not to allow a system to use certain functionality such as transdermal imaging. A user can choose whether or not to allow the system to determine their location. Depending on implementation, greater or fewer options can be set. For example, a user can be presented with options to choose a frequency for location updates or a duration of time in which the user allows a system to determine locations and send updates to a device. In some cases, options can be available to the user after enrollment.

In some implementations, heartbeat signatures may be used in conjunction with other identifying features. A shirt design, gait, or other feature can be used to locate a person. This can be used after initial heartbeat detection match. For example, a person wearing a red shirt can be tracked visually by cameras at a location. The use of the red shirt to track can be after a device of the user has been matched to a system using heartbeat signatures.

Stage C of FIG. 1 depicts a wearable device 111 on the person of user 110c sending a signal to a phone 113. The signal contains a heartbeat signature of user 110c. The phone 113 can send both the heartbeat signature and device details as part of a request 130 to the system 100. Device details could be any data, phone number, serial number, or unique identifier that could be used by system 100 to send data back to device 113.

In some implementations, a system can provide location updates to a device without requiring the device to provide device details. For example, a smartphone could send a synchronous request to a system including a heartbeat signature but no further identifying information. The system can respond to this request, on the same network connection, with a location of a person associated with the heartbeat signature.

In some implementations, a wearable device 111 can be replaced with another device. This device can detect heartbeat or bodily signature. For example, a phone could be used to detect a heartbeat directly. This could be done either natively in the system UI or through a third party application installed on the phone. The heartbeat signature and device data could similarly be sent in a data packet included in the request 130 to the system 100.

The heartbeat and locations shown in item 122 for person 1 (124), person 2 (126), and person 3 (128) represent the output from the visual data to heartbeat and location analyzer 120. Each heartbeat signature and location pair is a possible match for the user location request sent by device 113. Both the request 130 and camera data 122 are sent to a heartbeat matcher 140.

Stage D of FIG. 1 depicts the heartbeat matcher 140 inputting the request 130 together with camera data 122. Camera data 122 contains three heartbeat signatures along with a location. The heartbeat matcher can scan the three heartbeat signatures of items 124, 126, or 128 until a match is found. The heartbeat shown in item 128 matches the heartbeat shown in the request 130. The heartbeat matcher 140 takes the two matching signatures and can prepare output to be sent to the corresponding device. The heartbeat matcher 140 can send a signal to the device directly or delegate the task to another component of system 100.

In some implementations, the system can store data relevant to the location request process. The data storage can be used to keep track of user location and device identity. For example, the match of item 128 and the request 130 could be kept within data storage. If device 113 requested a location again, the system could use data from the stored match to aid in the process. Stored data could be used instead of, or in addition to, any user data sent with a request.

Stage E of FIG. 1 shows the heartbeat matcher 140 sending the location, Location Z, extracted from matched item 128 to the corresponding device 113 of the request 130. The heartbeat matcher 140 can use data within the request 130 to communicate the location of user 110c. The location of user 110c can be sent to device 113 or other device. For example, based on user settings or system settings, the location of user 110c can be sent to another device associated with device 113 or user 110c.

The location sent as a response to the request of device 113 can be in various location identity forms (e.g., street address, coordinates, landmarks, other signifiers).

In some implementations, the system 100 may respond to the user location request without needing a user heartbeat. In situations where a match has been made, it may be advantageous to use previous matches stored on the system instead of re-determining. For example, in applications like navigation which may require multiple user requests, stored data can improve the efficiency of system 100. Location retrieval can be a step, or multiple steps, within software to track a user and direct them to a particular destination. The software may use graphics to show the location received from system 100 within a known map of a building or physical space. The software may then determine a possible route which would lead the user to the particular destination. Location requests to a system could be used throughout navigation for up to date location tracking.

Figure 2:
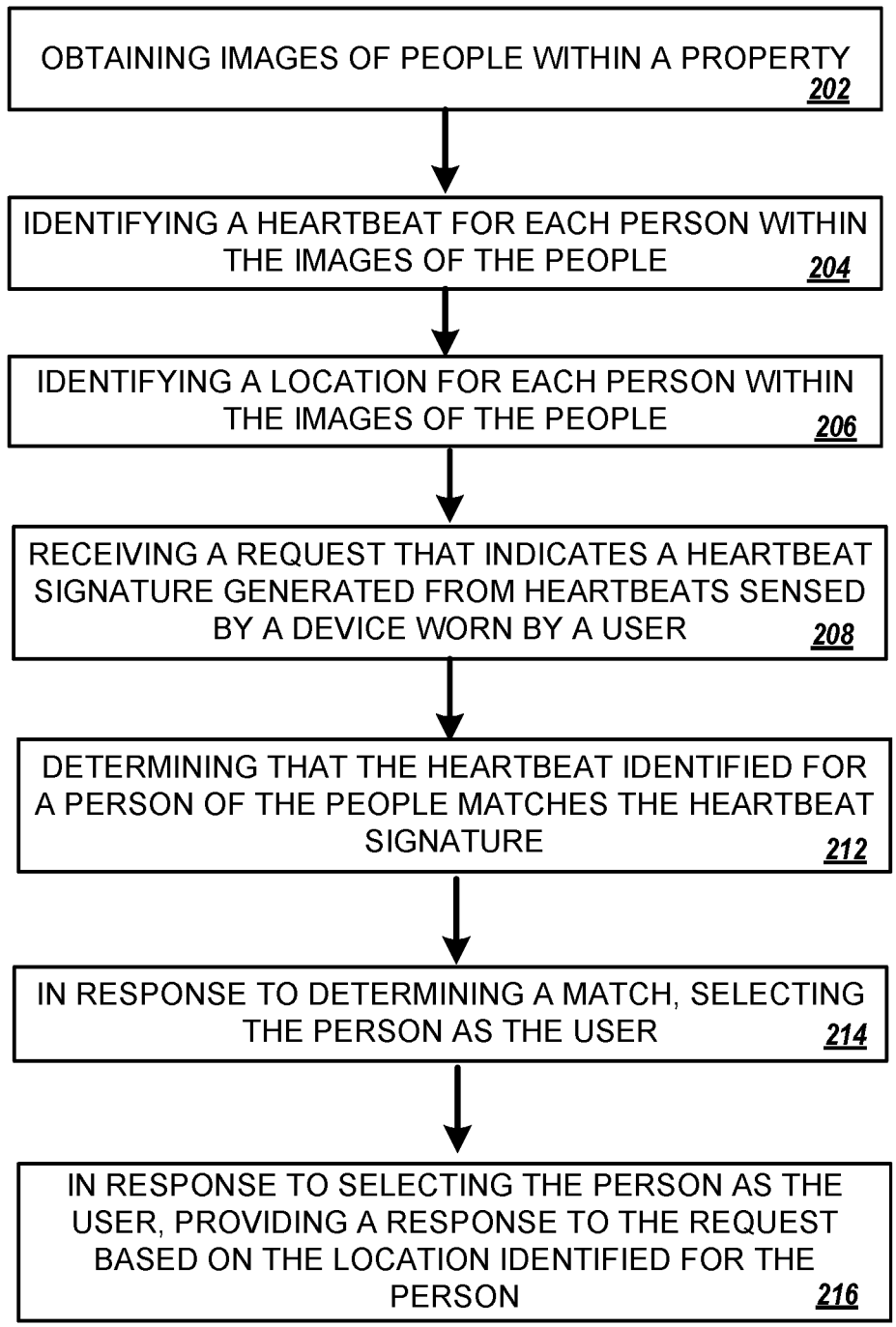
FIG. 2 is a flow diagram illustrating an example of a process for location tracking.

FIG. 2 is a flow diagram illustrating an example of a process 200 for location tracking. The process 200 may be performed by one or more electronic systems, for example, the system 100 of FIG. 1.

The process of 200 includes obtaining images of people within a property (202). For example, the camera 105 located on the property 101 may be turned on and positioned such that the three persons 110a, 110b and 110c are within the camera's field of view and images are captured.

The process of 200 includes identifying a heartbeat for each person within the images of the people (204). For example, visual data captured from the camera 105 can be processed by the visual data to heartbeat and location analyzer 120 to detect persons within the images of the people and heartbeat signatures for the persons within the images of the people.

In some implementations, transdermal data is used to identity a heartbeat for a person within the images of the people. For example, the camera 105, or another sensor affixed or otherwise communicably connected to the camera 105, can obtain transdermal data such as the timing and relative quantity of blood flowing in the veins of the person. In some implementations, the camera 105, or another sensor affixed or otherwise communicably connected to the camera 105, is a transdermal camera capable of detecting transdermal data including elements beneath the skin of the person. For example, the camera 105 can detect a pattern of blood flow of the person which can then be used to identify the heartbeat of the person. The blood flow can show periodic increase and decrease of blood flow through the veins of the person. Based on the periodic increase and decrease of the blood flow, a heart rate corresponding to the heartbeat of the person can be identified.

In some implementations, transdermal data includes data obtained from a laser. For example, a laser can be used to obtain transdermal data that can be used by a system, such as the system 100, to determine, based on the transdermal data, the heartbeat of a person at a distance. The laser can obtain the transdermal data by detecting movement caused by blood flow within the person. Periods within detected movements caused by the blood flow can be used to identify a heartbeat of the person.

In some implementations, elements of the cardiac cycle corresponding to a heartbeat of a person are used to identity a heartbeat for a given person. For example, values corresponding to transdermal data that represent magnitudes of blood flow increase and decrease can be used to determine specific elements of a cardiac cycle including specific processes of the heart that affect patterns of blood flow such as isovolumic relaxation, inflow or ventricular filling, isovolumic contraction, and ejection or ventricular ejection, among others. Each element of the cardiac cycle can then be described within one or more values corresponding to a pattern of blood flow. For example, a scale can be established from 0 to 1 and higher blood flow rate can correspond to the value 1 and lower blood flow rate can correspond to the value 0. A series of values over time can then be used to describe the heartbeat of a person including the elements of one or more cardiac cycles.

The process of 200 includes identifying a location for each person within the images of the people (206). For example, the camera 105 can be calibrated such that each pixel within a given field of view can be mapped to a physical space. The visual data can include at least one representation of a person as one or more groups of pixels within the images of the people. In some implementations, video footage is used to capture the images of the people. Visual analysis can map the pixels representing a person to a physical space at a location. For example, the visual data to heartbeat and location analyzer 120 can use visual data to determine the physical location of persons.

In some implementations, pixel mapping is used to determine the location of the given person within the images of the people. For example, the camera 105 can obtain visual data of a scene of the property that includes a representation of a person. The pixels representing the person, or pixels adjacent to the representation of the person, can be mapped to a physical location of the property. The mapping can be dynamic based on known locations of elements within a given scene captured by the camera 105 or can be static where specific regions of the given scene are pre-mapped to physical locations. For example, a camera can be stationary and capture a scene of a gate in an airport where each pixel can be pre-mapped to a physical location of the corresponding gate in the airport. For another example, a camera can move and capture a range of scenes including the gate in the airport. The moving camera can determine physical locations corresponding to the gate in the airport by visual detecting elements related to the gate, such as a gate sign or any other physical feature, and then determine the location of target elements, such as a person in the images of the people, based on a determined distance to the predetermined locations of known elements, such as the gate sign, identified through visual detection.

In some implementations, a location is indicated by one or more geographical coordinates. For example, the location of the given person within the images of the people can be indicated by a first value representing latitude and a second value representing longitude. Similarly, other coordinate systems, such as Cartesian coordinates or the like may be used.

The process of 200 includes receiving a request that indicates a heartbeat signature generated from heartbeats sensed by a device worn by a user (208). For example, the wearable device 111 can detect the heartbeat of the user 110c. The detected heartbeat can be sent by another device, or the wearable device 111, as part of a data stream together with the location request.

In some implementations, before receiving the request, an identified heartbeat or location is stored. For example, as a result of identifying a heartbeat for each person within the images of the people and as a result of identifying a location for each person within the images of the people, the system 100 can store one or more identified heartbeats or locations of one or more persons in data storage. In this way, the system 100 can receive a request and compare data of the request to data obtained from the data storage. The data can be stored for any period of time to allow for a request to be responded to at any time.

In some implementations, the request includes a visual identifier. For example, a visual identifier can include an elements of an outfit worn by a person, hair color, age, gait, or any other visual element of their appearance. The visual identifier can then be used to determine if a given person is the user. In some cases, the visual identifier is used with heartbeat matching in order to determine if the given person is the user. For example, first, visual identifiers can discard persons of the images that do not match the criteria of the visual identifier. Then, heartbeat matching can determine which person of the remaining persons is the user. Of course, in some cases, heartbeat matching is performed before visual identifier matching. For example, if a heartbeat matching determines that two heartbeats corresponding to two different persons are each similar to the heartbeat signature of the request, such as if the two heartbeats are each within a predetermined threshold of the heartbeat signature, the visual identifier or other additional data of the request can be used to determine which of the two persons is the user.

In some implementations, the request includes a device identifier. For example, a device identifier corresponding to a user device can be used such that the system 100 is able to send a return message to the user device, such as the mobile computing device 113. The device identifier can be used to encrypt or otherwise provide data to the mobile computing device 113.

In some implementations, the device worn by the user directly sends the request to the system 100. For example, the wearable device 111 can be used to send a request, such as the request 130, to the heartbeat matcher 140 of the system 100 without first sending a signal to the mobile computing device 113. The request can include a device identifier of either the wearable device 111 or another device, such as the mobile computing device 113, such that the system 100 can send response data to a device corresponding to the device identifier.

The process of 200 includes determining that the heartbeat identified for a person of the people matches the heartbeat signature (212). For example, the heartbeat matcher 140 of FIG. 1 can analyze the heartbeats of each person of the people at location 101. Each person's heartbeat can be compared to the user heartbeat of the request 130. A match can be made by comparing analyses of the heartbeats of each person (e.g., item 124, item 126, item 128) and the heartbeat of the user of the request 130.

In some implementations, elements of a cardiac cycle are used to determine if the heartbeat identified for the person of the people matches the heartbeat signature. For example, as described above, patterns of blood flow can be used to determine elements of a cardiac cycle. A series of values representing blood flow rate over time can be used to describe the heartbeat identified for the person and the heartbeat signature. Based on comparing one or more cardiac cycles of the heartbeat identified for the person and the heartbeat signature, the heartbeat matcher 140 of FIG. 1 can determine if the person is the user corresponding to the heartbeat signature of the request.

In some implementations, the heartbeat identified for the person of the people matches the heartbeat signature based on one or more values corresponding to the heartbeat identified for the person and the heartbeat signature. For example, a predetermined threshold can be used to determine if values corresponding to elements of the cardiac cycle are within a predetermined tolerance from one another. In some implementation, an algorithm, such as a machine learning algorithm, is trained to match sets of heartbeats. For example, a set of two heartbeat signals that are known to be from the same person can be used as input for the machine learning algorithm. The machine learning algorithm can be trained to detect various relationships corresponding to time or magnitude of specific periods of blood flow corresponding to the cardiac cycle. For example, an isovolumic contraction represented by values corresponding to the heartbeat identified for the person can be determined as similar to another isovolumic contraction of the heartbeat signature such that the heartbeat matcher 140 determines that the heartbeat identified for the person of the people matches the heartbeat signature.

The process of 200 includes selecting the person as the user in response to determining a match (214). For example, the heartbeat matcher 140, upon determining a match between the user heartbeat of the request 130 and the heartbeat item 128 of the visual data to heartbeat and location analyzer output 122, can select person 110c as the user. In some implementations, a database of current users can be used to track current users. The database can be amended and the person recently matched can be added to the database.

The process of 200 includes providing a response to the request based on the location identified for the person in response to selecting the person as the user (216). For example, at the location 101, the user 110c who requests their location may be presented with a notification on the mobile computing device 113 detailing that the user 110c is at location Z (step E of FIG. 1). The location provided in response to a request can be in various forms (e.g., coordinates, landmark identifiers, street addresses).

In some implementations, the response to the request includes a location of the person. For example, the heartbeat matcher 140 of FIG. 1 can send a location corresponding to the location of the user 110c to the mobile computing device 113. In some cases, the location of the user 110c can be used by an application of the mobile computing device 113 to provide a visual representation of the location of the user 110c in reference to a map of the property. In some cases, the application of the mobile computing device 113 can provide directions for the user from one area of a property, such as a first gate of an airport, to another area of the property, such as a second gate of an airport for a connecting flight. The location of the user 110c provided by the heartbeat matcher 140 of the system 100 can be used to track the progress of the user 110c as the user 110c proceeds to their destination.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A computer-implemented method comprising:
   obtaining images of one or more persons within a property;
   identifying a heartbeat for each person of the one or more persons within the images of the one or more persons;
   identifying a location for each person within the images;
   receiving a request that indicates a heartbeat signature generated from heartbeats sensed by a device worn by a user;
   determining that an identified heartbeat of a person of the one or more persons matches the heartbeat signature;
   in response to determining that the identified heartbeat of the person of the one or more persons matches the heartbeat signature, selecting the person as the user; and
   in response to selecting the person as the user, providing a response to the request based on a location of the person.

2. The method of claim 1, wherein the images comprise transdermal data of the one or more persons and identifying a heartbeat for each person of the one or more persons within the images of the one or more persons comprises:
   using the transdermal data of the one or more persons to determine patterns of blood flow; and
   in response to determining the patterns of blood flow, identifying a heartbeat for each person of the one or more persons.

3. The method of claim 1, wherein the images comprise a first portion of one or more pixels that represent a first person and identifying a location for each person within the images comprises:
   determining the first portion of the one or more pixels correspond to a physical location of the property and the first portion of the one or more pixels represent at least a portion of the first person; and
   identifying the physical location of the property as a location of the first person of the one or more persons.

4. The method of claim 3, wherein the physical location of the property is indicated by one or more geographical coordinates.

5. The method of claim 1, further comprising, before receiving the request, storing the identified heartbeat of the person within data storage, wherein determining that the identified heartbeat of the person of the one or more persons matches the heartbeat signature comprises:
   obtaining the identified heartbeat from the data storage; and
   comparing the heartbeat signature of the request to the identified heartbeat from the data storage to determine that the identified heartbeat of the person of the one or more persons matches the heartbeat signature.

6. The method of claim 1, wherein determining that the identified heartbeat of the person of the one or more persons matches the heartbeat signature comprises:
   obtaining a first portion of the identified heartbeat and a second portion of the heartbeat signature, wherein the first portion comprises at least a representation of a first heartbeat and the second portion comprises at least a representation of a second heartbeat;
   determining that elements of a first cardiac cycle corresponding to the representation of the first heartbeat match elements of a second cardiac cycle corresponding to the representation of the second heartbeat; and
   determining that the identified heartbeat of the person of the one or more persons matches the heartbeat signature based at least on determining that the elements of the first cardiac cycle corresponding to the representation of the first heartbeat match the elements of the second cardiac cycle corresponding to the representation of the second heartbeat.

7. The method of claim 1, wherein the request comprises at least one visual identifier of the user that is used in selecting the person as the user.

8. The method of claim 1, wherein the request comprises a device identifier corresponding to a user device, and wherein providing the response to the request comprises:
   providing the response to the user device based on the device identifier.

9. The method of claim 1, wherein the device worn by the user is a smart watch that senses blood flow within blood vessels of the user.

10. The method of claim 1, wherein the request is received from the device worn by the user.

11. The method of claim 1, wherein the device worn by the user is communicably connected to a mobile device of the user and the request is received from the mobile device of the user.

12. The method of claim 1, wherein the property is an airport.

13. The method of claim 1, wherein the response to the request is used to provide the location of the person within the property to a mapping application operating on a user device.

14. A system comprising one or more computers and one or more storage devices on which are stored instructions that are operable, when executed by the one or more computers, to cause the one or more computers to perform operations comprising:

obtaining images of one or more persons within a property;

identifying a heartbeat for each person of the one or more persons within the images of the one or more persons;

identifying a location for each person within the images;

receiving a request that indicates a heartbeat signature generated from heartbeats sensed by a device worn by a user;

determining that an identified heartbeat of a person of the one or more persons matches the heartbeat signature;

in response to determining that the identified heartbeat of the person of the one or more persons matches the heartbeat signature, selecting the person as the user; and in response to selecting the person as the user, providing a response to the request based on a location of the person.

15. The system of claim 14, wherein the images comprise transdermal data of the one or more persons and identifying a heartbeat for each person of the one or more persons within the images of the one or more persons comprises:

using the transdermal data of the one or more persons to determine patterns of blood flow; and in response to determining the patterns of blood flow, identifying a heartbeat for each person of the one or more persons.

16. The system of claim 14, wherein the images comprise a first portion of one or more pixels that represent a first person and identifying a location for each person within the images comprises:

determining the first portion of the one or more pixels correspond to a physical location of the property and the first portion of the one or more pixels represent at least a portion of the first person; and identifying the physical location of the property as a location of the first person of the one or more persons.

17. The system of claim 16, wherein the physical location of the property is indicated by one or more geographical coordinates.

18. The system of claim 14, further comprising, before receiving the request, storing the identified heartbeat of the person within data storage, wherein determining that the identified heartbeat of the person of the one or more persons matches the heartbeat signature comprises:

obtaining the identified heartbeat from the data storage; and comparing the heartbeat signature of the request to the identified heartbeat from the data storage to determine that the identified heartbeat of the person of the one or more persons matches the heartbeat signature.

19. The system of claim 14, wherein determining that the identified heartbeat of the person of the one or more persons matches the heartbeat signature comprises:

obtaining a first portion of the identified heartbeat and a second portion of the heartbeat signature, wherein the first portion comprises at least a representation of a first heartbeat and the second portion comprises at least a representation of a second heartbeat;

determining that elements of a first cardiac cycle corresponding to the representation of the first heartbeat match elements of a second cardiac cycle corresponding to the representation of the second heartbeat; and determining that the identified heartbeat of the person of the one or more persons matches the heartbeat signature based at least on determining that the elements of the first cardiac cycle corresponding to the representation of the first heartbeat match the elements of the second cardiac cycle corresponding to the representation of the second heartbeat.

20. A non-transitory computer storage medium encoded with instructions that, when executed by one or more computers, cause the one or more computers to perform operations comprising:

obtaining images of one or more persons within a property;

identifying a heartbeat for each person of the one or more persons within the images of the one or more persons;

identifying a location for each person within the images;

receiving a request that indicates a heartbeat signature generated from heartbeats sensed by a device worn by a user;

determining that an identified heartbeat of a person of the one or more persons matches the heartbeat signature;

in response to determining that the identified heartbeat of the person of the one or more persons matches the heartbeat signature, selecting the person as the user; and in response to selecting the person as the user, providing a response to the request based on a location of the person.

* * * * *